US009179074B2

(12) United States Patent
Yasuda

(10) Patent No.: US 9,179,074 B2
(45) Date of Patent: Nov. 3, 2015

(54) ENDOSCOPE DEVICE

(75) Inventor: Hiroaki Yasuda, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 893 days.

(21) Appl. No.: 13/239,562

(22) Filed: Sep. 22, 2011

(65) Prior Publication Data

US 2012/0075449 A1 Mar. 29, 2012

(30) Foreign Application Priority Data

Sep. 29, 2010 (JP) ................................. 2010-219437

(51) Int. Cl.
*H04N 5/235* (2006.01)
*A61B 1/00* (2006.01)
*A61B 1/04* (2006.01)
*A61B 1/045* (2006.01)
*A61B 1/06* (2006.01)
*H04N 5/225* (2006.01)

(52) U.S. Cl.
CPC .......... *H04N 5/2354* (2013.01); *A61B 1/00009* (2013.01); *A61B 1/043* (2013.01); *A61B 1/045* (2013.01); *A61B 1/063* (2013.01); *A61B 1/0638* (2013.01); *A61B 1/0653* (2013.01); *A61B 1/0661* (2013.01); *H04N 2005/2255* (2013.01)

(58) Field of Classification Search
CPC .... A61B 1/00009; A61B 1/043; A61B 1/045; A61B 1/063; A61B 1/0638; A61B 1/0653; A61B 1/0661; H04N 2005/2255; H04N 5/2354
USPC .......................................................... 348/68
See application file for complete search history.

(56) References Cited

U.S. PATENT DOCUMENTS

| 5,001,556 A * | 3/1991 | Nakamura et al. ............... 348/70 |
| 2002/0014595 A1* | 2/2002 | Sendai et al. ............... 250/458.1 |
| 2003/0001951 A1* | 1/2003 | Tsujita et al. ................... 348/65 |
| 2003/0176768 A1 | 9/2003 | Gono et al. |

(Continued)

FOREIGN PATENT DOCUMENTS

| CN | 101584572 A | 11/2009 |
| JP | 3559755 B2 | 9/2004 |
| JP | 3607857 B2 | 1/2005 |

OTHER PUBLICATIONS

Chinese Office Action and Search Report dated Jul. 3, 2014, issued in Chinese Application No. 201110303479.2, with English translation thereof.

*Primary Examiner* — Sath V Perungavoor
*Assistant Examiner* — Peter D Le
(74) *Attorney, Agent, or Firm* — Birch, Stewart, Kolasch & Birch, LLP

(57) ABSTRACT

The endoscope device includes a light source control section that controls emission of a narrow band light from a first light source section and a wide band light from a second light source section and light emission amounts of the narrow and wide band light, an imaging section that captures an image of a subject using returned light from the subject, a light amount calculating section that calculates a capturing light amount, a light amount ratio calculating section that calculates a ratio between light emission amounts of the narrow and wide band light, and an image processing section that performs a predetermined image processing. The light source control section controls the light emission amounts in accordance with the capturing light amount and the image processing section changes an image processing condition for adjusting a color tint in accordance with the ratio.

8 Claims, 5 Drawing Sheets

(56) References Cited

U.S. PATENT DOCUMENTS

| | | |
|---|---|---|
| 2004/0186351 A1* | 9/2004 | Imaizumi et al. .............. 600/160 |
| 2007/0078299 A1* | 4/2007 | Ayame et al. ................. 600/101 |
| 2007/0088192 A1* | 4/2007 | Takeuchi et al. .............. 600/101 |
| 2008/0174701 A1* | 7/2008 | Iketani et al. ................. 348/687 |
| 2008/0281154 A1 | 11/2008 | Gono et al. |
| 2008/0283770 A1* | 11/2008 | Takahashi .................. 250/458.1 |
| 2009/0065679 A1* | 3/2009 | Tanimoto ................... 250/208.1 |
| 2009/0149706 A1* | 6/2009 | Yamazaki et al. ............ 600/109 |
| 2009/0289200 A1* | 11/2009 | Ishii ........................... 250/459.1 |
| 2010/0268091 A1* | 10/2010 | Takaoka ........................ 600/478 |
| 2011/0237895 A1* | 9/2011 | Yoshida et al. ............... 600/180 |

* cited by examiner

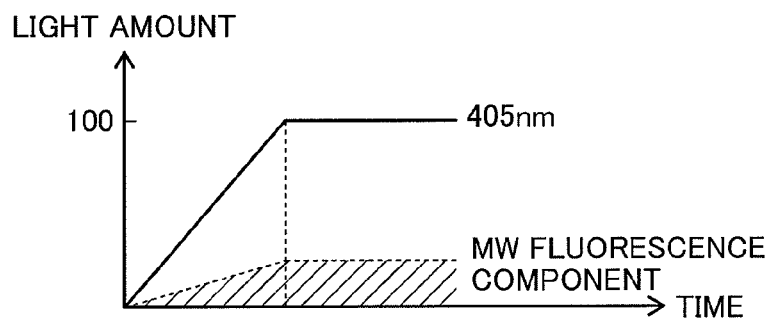
FIG. 4A
FIG. 4B
FIG. 5
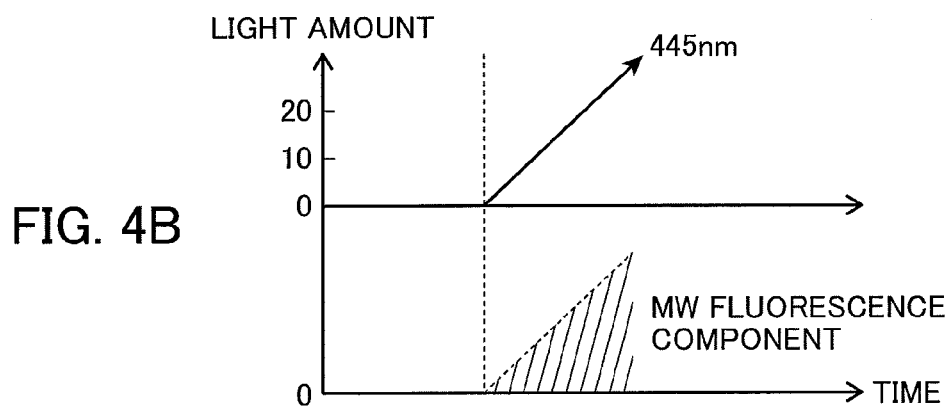
| LIGHT AMOUNT RATIO (405LD:445LD) | COLOR CONVERSION COEFFICIENT TABLE | | |
|---|---|---|---|
| | KR | KG | KB |
| 100 : 0 | R00 | G00 | B00 |
| 100 : 1 | R01 | G01 | B01 |
| 100 : 2 | R02 | G02 | B02 |
| ⋮ | ⋮ | ⋮ | ⋮ |
| 100 : 10 | R10 | G10 | B10 |
| ⋮ | ⋮ | ⋮ | ⋮ |
| 100 : 20 | R20 | G20 | B20 |
| ⋮ | ⋮ | ⋮ | ⋮ |

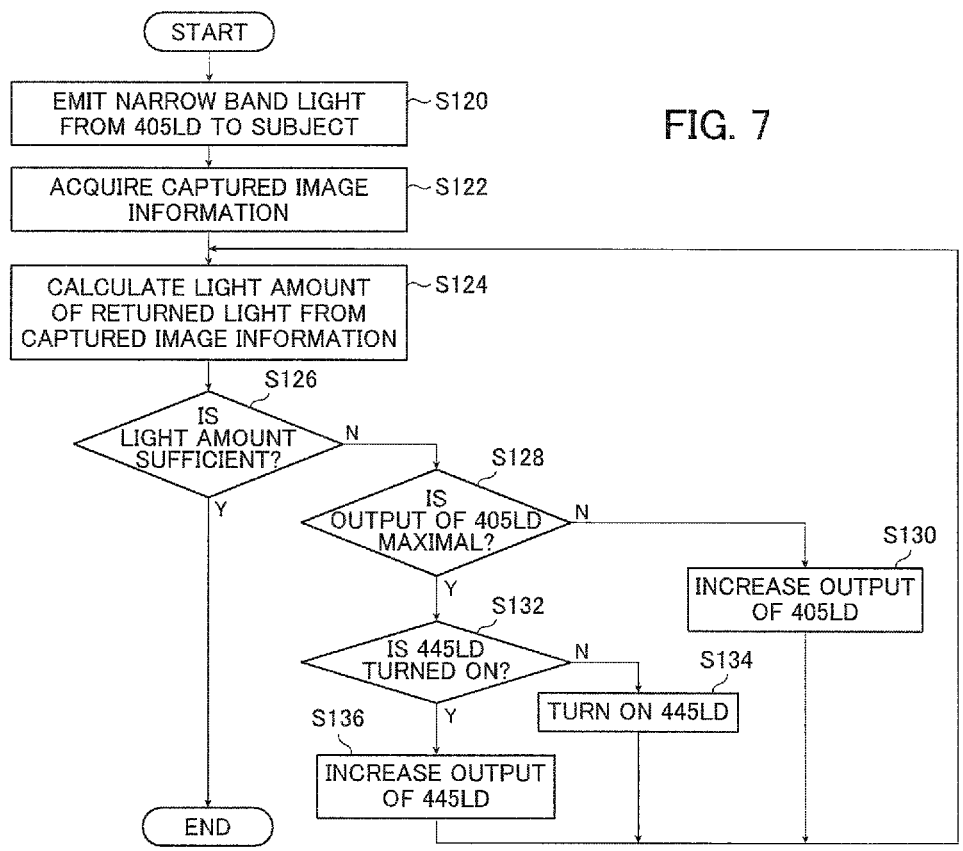

ENDOSCOPE DEVICE

BACKGROUND OF THE INVENTION

The present invention relates to an endoscope device capable of performing a special light observation using specific narrow band light and wide band light such as white illumination light.

In recent years, an endoscope device capable of performing a so-called special light observation has been used, where the special light observation obtains information on a tissue at a desired depth of a living body by emitting specific narrow band light (narrow band light) to a mucous tissue of the living body. This type of endoscope device may simply visualize living body information, which cannot be obtained from an ordinary observation image, by emphasizing a lesion and a microstructure of a surface layer of a new blood vessel generated at, for example, a mucous layer or a lower mucous layer. For example, when an observation subject is a cancer lesion, if narrow band blue light (B) is emitted to the mucous layer, the microstructure or the microscopic blood vessel of the surface layer of the tissue may be observed in more detail, so that the lesion may be more accurately diagnosed.

On the other hand, an invasion depth of light in the thickness direction of the living body tissue is dependent on the wavelength of the light. In the case of the blue light (B) having a short wavelength, the light only reaches the vicinity of the surface layer due to the absorbing and scattering characteristics of the living body tissue, and is absorbed and scattered at the depth range, so that the light may be observed as returned light mainly including information on the surface layer tissue. In the case of green light G having a wavelength longer than that of the B light, the light reaches a position deeper than the range the B light reaches, and is absorbed and scattered at this range, so that the light may be observed as returned light mainly including information on the intermediate layer tissue and the surface layer tissue. In the case of red light (R) having a wavelength longer than that of the G light, the light reaches a deeper position of the tissue, and is absorbed and scattered at this range, so that the light may be observed as returned light mainly including information on the deep layer tissue and the intermediate layer tissue.

That is, image signals obtained by receiving light using an imaging sensor such as a CCD after emitting the B light, the G light, and the R light respectively mainly include information on the surface layer tissue, information on the intermediate layer tissue and the surface layer tissue, and information on the deep layer tissue and the intermediate layer tissue.

For this reason, in the special light observation, in order to easily observe the microstructure or the microscopic blood vessel of the tissue surface layer of the living body tissue, only two types of narrow band light, that is, the narrow band light of blue (B) suitable for observing the surface layer tissue and the narrow band green light G suitable for observing the intermediate layer tissue and the surface layer tissue are used as the narrow band light emitted to the living body tissue without using the narrow band red light R mainly suitable for observing the intermediate layer tissue and the deep layer tissue of the living body tissue. Then, image processing is performed only using a B-image signal (B narrow band data) mainly including information on the surface layer tissue and obtained by an imaging sensor after emitting the B narrow band light and a G-image signal (G narrow band data) mainly including information on the intermediate layer tissue and the surface layer tissue and obtained by an imaging sensor after emitting the G narrow band light, and an observation is performed by displaying a quasi-color image on a monitor or the like.

Therefore, in the image processing, the G-image signal (G narrow band data) obtained by the imaging sensor is allocated to R-image data of a color image through a predetermined coefficient, the B-image signal (B narrow band data) is allocated to G-image data and B-image data of a color image through a predetermined coefficient, a quasi-color image including 3-ch (channel) color image data is created, and the image is displayed on a monitor or the like.

For this reason, the image processing of the narrow band light mode converting two GB-image signals obtained by receiving the returned light of the narrow band light using the imaging sensor into RGB color image data for a quasi-color display on a display unit is different from the image processing of the ordinary light mode converting three RGB-image signals obtained by receiving the returned light of the ordinary light using the imaging sensor into RGB color image data for a color display on a display unit.

Further, even in the special light observation using the R narrow band light, the G narrow band light, and the B narrow band light, when the microstructure or the microscopic blood vessel of the surface layer tissue is observed, as described above, the image processing is performed only by using the G-image signal and the B-image signal without using the R-image signal (R narrow band data), and an observation is performed by displaying the quasi-color image on the monitor or the like.

Even in this case, in the image processing, in the same manner, the G-image signal is allocated to the R-image data, and the B-image signal is allocated to the G-image data and the B-image data, the quasi-color image including 3-ch color data is created, and the image is displayed on the monitor or the like.

As a result, in any case, since the quasi-color image displayed on the monitor or the like mainly includes the B-image signal (B narrow band data) including information on the surface layer tissue, the microstructure or the microscopic blood vessel of the surface layer tissue may be displayed in more detail, and the microstructure and the microscopic blood vessel of the surface layer tissue may be easily observed (refer to JP 3559755 B and JP 3607857 B).

In the special light observation described above, when the distance between the lesion tissue and the special light irradiation position is small, the microstructure or the microscopic blood vessels of the surface layer tissue, which may be easily brightly seen, may be displayed as an image, but there is a problem in that it is more difficult to see the microstructure or the microscopic blood vessels of the surface layer tissue as the distance increases.

Further, when the distance increases as described above, the irradiation light amount is generally increased in order to handle such a problem. However, there is a limitation on the increase in irradiation light amount, particularly, an increase in special light amount. Accordingly, a problem arises in that the color tint of the captured image changes when compensating for insufficient special light amount using ordinary light.

SUMMARY OF THE INVENTION

It is an object of the invention to provide an endoscope device capable of obtaining a captured image, which is bright and has stable color tint or hue all the time, without any limitation on capturing distance when observing the structures and components of a living body such as surface layer microscopic blood vessels, where the device does not cause an operator to intentionally adjust the irradiation light amount while checking a captured image even in ordinary observation and special light observation.

In order to solve the above-described problems, according to the present invention, there is provided an endoscope device comprising: a first light source section that emits narrow band light having a predetermined wavelength bandwidth narrowed in accordance with spectral spectrum characteristics of a structure and a component of a living body as a subject; a second light source section that emits wide band light having a wide wavelength bandwidth including a visible region; a light source control section that controls emission of the narrow band light from the first light source section and the wide band light from the second light source section and light emission amounts of the narrow band light and the wide band light; an imaging section that captures an image of the subject using returned light in which at least one of the narrow band light and the wide band light emitted to the subject is returned from the subject and outputs captured image information; a light amount calculating section that calculates a capturing light amount of the captured image from the captured image information captured by the imaging section; a light amount ratio calculating section that calculates a ratio between a light emission amount of the narrow band light emitted from the first light source section and a light emission amount of the wide band light emitted from the second light source section controlled by the light source control section; and an image processing section that performs a predetermined image processing on the captured image information, wherein the light source control section controls the light emission amount of the narrow band light emitted from the first light source unit and the light emission amount of the wide band light emitted from the second light source section in accordance with the capturing light amount calculated by the light amount calculating section, and wherein the image processing section changes an image processing condition for adjusting a color tint of the captured image in accordance with the ratio between the light emission amount of the narrow band light and the light emission amount of the wide band light calculated by the light amount ratio calculating section.

In this case, it is preferable that the light source control section perform different controls in accordance with the capturing light amount calculated by the light amount calculating section such that: in case of a capturing operation using the narrow band light, emission of the wide band light from the second light source section is stopped and then the light emission amount of the narrow band light emitted from the first light source section is controlled and, when the light emission amount of the narrow band light becomes maximal, the wide band light is emitted from the second light source section and then the light emission amount of the wide band light is controlled, and in case of a capturing operation without using the narrow band light, emission of the narrow band light from the first light source section is stopped and then the light emission amount of the wide band light emitted from the second light source section is controlled.

In addition, it is preferable that the light source control section control at least one of the light emission amount of the narrow band light from the first light source section and the light emission amount of the wide band light from the second light source section so that the capturing light amount calculated by the light amount calculating section become a predetermined value or more necessary for capturing the subject regardless of a distance between the imaging section and the subject.

In addition, it is preferable that the light source control section control at least one of the light emission amount of the narrow band light from the first light source section and the light emission amount of the wide band light from the second light source section so that the capturing light amount calculated by the light amount calculating section substantially become equal to a predetermined value necessary for capturing the subject regardless of a distance between the imaging section and the subject.

In addition, it is preferable that, in case of a capturing operation using the narrow band light, the light source control section control such that: when the emission of the wide band light from the second light source section be stopped and the narrow band light be emitted from the first light source section, the light emission amount of the narrow band light emitted from the first light source section be controlled so that the capturing light amount of the captured image calculated by the light amount calculating section become equal to or more than a predetermined value necessary for capturing the subject, when the capturing light amount do not reach the predetermined value even when the light emission amount of the narrow band light become maximal, the narrow band light be emitted from the first light source section at a maximal light amount, and the wide band light be emitted from the second light source section and then, the light emission amount of the wide band light be controlled so that the capturing light amount become equal to or more than the predetermined value, and the narrow band light be emitted from the first light source section and the wide band light be emitted from the second light source section, the light emission amount of the wide band light be controlled so that the capturing light amount becomes the predetermined value or more.

In addition, it is preferable that, in case of a capturing operation without using the narrow band light in which the emission of the narrow band light from the first light source section be stopped and the wide band light is emitted from the second light source section, the light source control section controls the light emission amount of the wide band light emitted from the second light source section so that the capturing light amount of the captured image calculated by the light amount calculating section becomes the predetermined value or more.

In addition, it is preferable that, in case of a capturing operation using the narrow band light, when a distance between the imaging section and the subject be set to a predetermined distance in case where the capturing light amount be the predetermined value when the light emission amount of the narrow band light emitted from the first light source section controlled by the light source control section become maximal, the light source control section allow the imaging section to perform a capturing operation using only the narrow band light in a near-distance capturing operation in which the distance between the imaging section and the subject be smaller than the predetermined distance, and the light source control section allow the imaging section to perform a capturing operation using the narrow band light and the wide band light in a far-distance capturing operation in which the distance between the imaging section and the subject be larger than the predetermined distance.

In addition, it is preferable that, in case of a capturing operation without using the narrow band light, the light source control section allow the imaging section to perform a capturing operation using only the wide band light.

In addition, it is preferable that the light amount ratio calculating section calculate a ratio between the light emission amount of the narrow band light and the light emission amount of the wide band light based on values of electrical currents passed through the first light source section and the second light source section by the light source control section.

In addition, it is preferable that the image processing section include a color conversion coefficient table representing a relationship between a color conversion coefficient for adjusting a color tint of the captured image and a ratio between the light emission amount of the narrow band light and the light emission amount of the wide band light obtained in advance so that a white balance of the captured image do not change, in order to change the image processing condition, and the image processing section select the color conversion coefficient from the color conversion coefficient table based on the ratio between the light emission amount of the narrow band light and the light emission amount of the wide band light calculated by the light amount calculating section.

Further, the invention provides an endoscope device including: a first light source section that emits first illumination light excellently acquiring information on a surface layer tissue of a living body as a subject; a second light source section that emits second illumination light mainly including white light excellently illuminating the subject; a light source control section that controls emission of the first illumination light from the first light source section and the second illumination light from the second light source section and a light emission amount of the first illumination light and the second illumination light; an imaging section that captures an image of the subject by returning light from at least one of the first illumination light and the second illumination light emitted to the subject and outputs captured image information; a light amount calculating section that calculates a capturing light amount of the captured image from the captured image information obtained by the imaging section; a light amount ratio calculating section that calculates a ratio between the light emission amount of the first illumination light emitted from the first light source section and the light emission amount of the second illumination light emitted from the second light source section controlled by the light source control section; and an image processing section that performs predetermined image processing on the captured image information, wherein the light source control section controls the light emission amount of the first illumination light emitted from the first light source section and the light emission amount of the second illumination light emitted from the second light source section in accordance with the capturing light amount calculated by the light amount calculating section, and wherein the image processing section changes an image processing condition for adjusting the color tint of the captured image in accordance with the ratio between the light emission amount of the first illumination light and the light emission amount of the second illumination light calculated by the light amount ratio calculating section.

According to the endoscope device of the invention, in the ordinary observation and the special light observation, the light emission conditions of the special light source and the white illumination light source are sequentially controlled so that the light amount of the returned light detected by the imaging element becomes a predetermined value or more at all times, and the image processing condition for adjusting the color tint (hue) of the image processing section is changed in accordance with the light emission conditions of the special light source and the white illumination light source. Accordingly, in the case of performing the ordinary observation and the special light observation, for example, even when the capturing operation is performed at a position far from or close to a lesion, the operator does not need to intentionally adjust the color tint of the captured image and the light emission conditions of the light sources while observing the captured image. Of course, in the ordinary observation and particularly in the special light observation for a lesion or surface layer microscopic blood vessels, a captured image with a stable color tint may be obtained at all times regardless of the capturing distance.

BRIEF DESCRIPTION OF THE DRAWINGS

FIGS. 4A and 4B are graphs respectively illustrating an example of a relation between an elapsed time and an emission light amount from a blue-violet laser beam source (405LD) and a blue laser beam source (445LD) shown in FIG. 3.

FIG. 5 is a graph illustrating an example of a color conversion table included in a special light color converting section of a special light image processing unit shown in FIG. 3.

FIG. 7 is a flowchart illustrating a flow of an example of an adjustment of a light amount of a light source unit shown in FIG. 1.

DETAILED DESCRIPTION OF THE INVENTION

Hereinafter, an endoscope device according to the invention will be described in detail through a preferred embodiment shown in the accompanying drawings.

Figure 1:
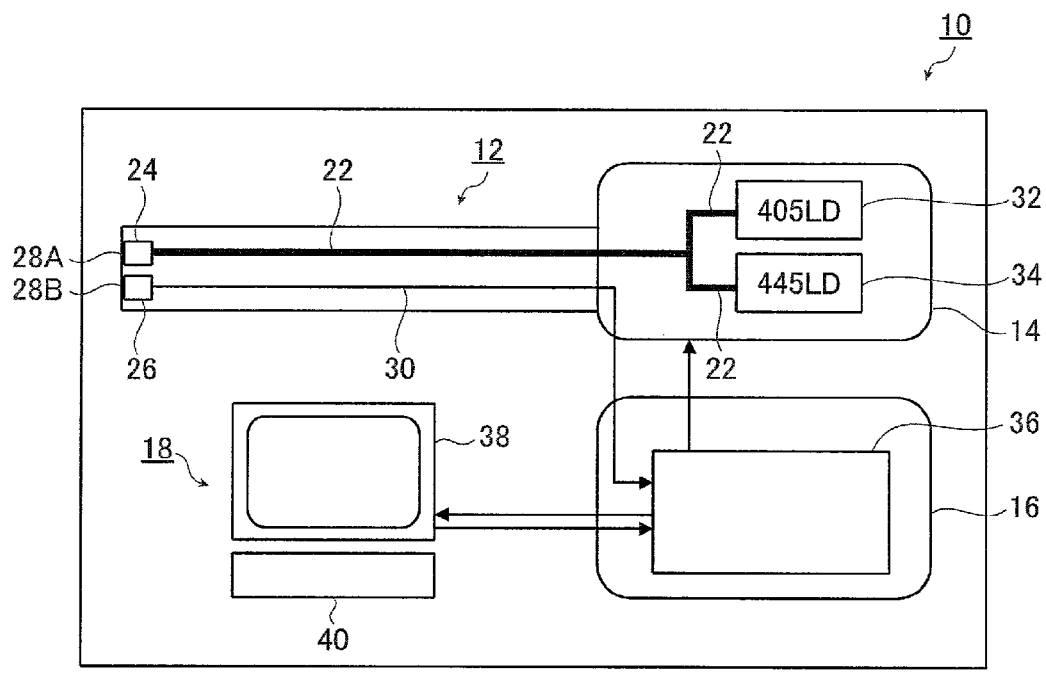
FIG. 1 is a block diagram schematically illustrating an example of an entire configuration of an endoscope device of an embodiment of the invention.

FIG. 1 is a block diagram schematically illustrating an example of an entire configuration of the endoscope device of the embodiment of the invention.

As shown in the same drawing, an endoscope device 10 of the invention includes an endoscope 12, a light source unit 14, a processor 16, and an input and output unit 18. Here, the light source unit 14 and the processor 16 constitute a control device of the endoscope 12, and the endoscope 12 is optically connected to the light source unit 14 and is electrically connected to the processor 16. Further, the processor 16 is electrically connected to the input and output unit 18. Then, the input and output unit 18 includes a display section (monitor) 38 that outputs and displays image information or the like, a recording section (recording device) 42 (refer to FIG. 3) that outputs image information or the like, and an input section (mode switching section) 40 that serves as a UI (user interface) receiving an input operation of function setting or mode switching for an ordinary observation mode (referred to as an ordinary light mode) or a special light observation mode (referred to as a special light mode).

The endoscope 12 is an electronic endoscope that includes an illumination optical system emitting illumination light from the front end thereof and an imaging optical system capturing an image of a subject observation region. Furthermore, although not shown in the drawings, the endoscope 12 includes an endoscope insertion section that is inserted into a subject, an operation section that is used to curve the front end of the endoscope insertion section or perform an observation, and a connector that attachably and detachably connects the endoscope 12 to the light source unit 14 and the processor 16 of the control device. Furthermore, although not shown in the drawings, the operation section and the endoscope insertion section are provided with various channels such as a clamp channel through which a tissue extracting treatment tool or the like is inserted or air and water supply channels.

As shown in FIG. 1, the front end of the endoscope 12 is provided with an irradiation port 28A that emits light to a subject observation region. Although it will be specifically described later, the irradiation port 28A is provided with an imaging element (sensor) 26 such as a CCD (Charge Coupled Device) image sensor or a CMOS (Complementary Metal-Oxide Semiconductor) image sensor that constitutes an illumination optical system, includes a fluorescent body 24 constituting a white light source, and acquires image information of the subject observation region at a light receiving portion 28B adjacent to the irradiation port 28A. The irradiation port 28A of the endoscope 12 is provided with a cover glass or a lens (not shown) constituting an irradiation optical system, the light receiving portion 28B is provided with a cover glass or a lens (not shown) constituting an illumination optical system, and a light receiving surface of the imaging element 26 of the light receiving portion 28B is provided with an objective lens (not shown) constituting an imaging optical system.

The endoscope insertion section may be freely curved by the operation of the operation section, may be curved at an arbitrary angle in an arbitrary direction in accordance with a portion or the like of the subject where the endoscope 12 is used, and may direct the observation direction of the irradiation port 28A and the light receiving portion 28B, that is, the imaging element 26 to a desired observation portion.

Furthermore, it is desirable that the imaging element 26 be a complementary color sensor or an imaging sensor including a color filter (for example, an RGB color filter or a complementary color filter) in the light receiving region, but it is more desirable to use an RGB color image sensor.

The light source unit 14 includes a light source, that is, a blue-violet laser beam source (405LD) 32 that has a central wavelength of 405 nm and is used as a special light source in the special light mode and a blue laser beam source (445LD) 34 that has a central wavelength of 445 nm and is used as a white illumination light source, for both the ordinary light mode and the special light mode. Furthermore, the blue-violet laser beam having a central wavelength of 405 nm output from the blue-violet laser beam source 32 has an excellent detecting property for a structure and a component of a living body since it is narrow band light having a wavelength bandwidth narrowed in accordance with the emission spectrum of the structure and components of the living body.

The light emission from the semiconductor light emitting elements of the light sources 32 and 34 is individually controlled by a light source control section 48 (refer to FIG. 3), and the light emission condition of each of the light sources 32 and 34, that is, the light amount ratio between the light emitted from the blue-violet laser beam source 32 and the light emitted from the blue laser beam source 34 may be freely changed.

As the blue-violet laser beam source 32 and the blue laser beam source 34, a broad area type InGaN laser diode, an InGaNAs laser diode, or a GaNAs laser diode may be used. Further, the light source may be configured as a light emitter such as a light emitting diode.

The laser beams emitted from the light sources 32 and 34 are respectively input to optical fibers 22 by a condensing lens (not shown), and are transmitted to the connector through a multiplexer (not shown). Furthermore, the invention is not limited thereto, and a configuration may be adopted in which the laser beams output from the light sources 32 and 34 are directly transmitted to the connector without using the multiplexer.

The laser beam, which is obtained by multiplexing the blue-violet laser beam having a central wavelength of 405 nm and the blue laser beam having a central wavelength of 445 nm and is transmitted to the connector, is propagated to the front end of the endoscope 12 by the optical fiber 22 constituting the illumination optical system. Then, the blue laser beam emits fluorescence by exciting the fluorescent body 24 as a wavelength converting member disposed at the light emission end of the optical fiber 22 of the front end of the endoscope 12. Further, a part of the blue laser beam is directly transmitted through the fluorescent body 24. Then, a part of the blue-violet laser beam excites the fluorescent body 24, but most of the beam is transmitted through the fluorescent body 24 without any excitation, so that it becomes illumination light of a narrow band wavelength (so-called narrow band light).

The optical fiber 22 is a multi-mode fiber, and an example thereof includes a thin fiber cable having a core diameter of 105 μm, a cladding diameter of 125 μm, and a diameter, including a protective layer as an outer coat, of ϕ0.3 to 0.5 mm.

The fluorescent body 24 includes a plurality of types of fluorescent bodies (for example, a YAG-based fluorescent body or a fluorescent body of BAM ($BaMgAl_{10}O_{17}$) or the like) absorbing a part of the blue laser beam and the blue-violet laser beam and emitting green to yellow light by being excited. Accordingly, white (quasi-white) illumination light is obtained by combining green to yellow excitation light using the blue laser beam and the blue-violet laser beam as excitation light and the blue laser beam and the blue-violet laser beam not absorbed by the fluorescent body 24 and transmitted therethrough. As in the configuration example, when the semiconductor light emitting element emitting the blue laser beam having a central wavelength of 445 nm is used as an excitation light source, it is possible to obtain high-intensity white light with high light emitting efficiency, easily adjust the intensity of white light, and suppress a change in the color temperature and chromaticity of the white light as small as possible.

The fluorescent body 24 may prevent flickering generated when displaying a dynamic image or overlapping of noise disturbing an imaging operation due to speckles generated by coherent of a laser beam. Further, it is desirable that the fluorescent body 24 be formed in consideration of a difference in refractive index between a fluorescent material constituting the fluorescent body and a fixing and solidifying resin forming a filling material. The particle diameter of the material of the fluorescent body and the filling material has small absorbing and great scattering with respect to light of an infrared region. Accordingly, it is possible to improve a scattering effect without degrading light intensity with respect to light of a red or infrared region, and reduce optical loss.

Figure 2:
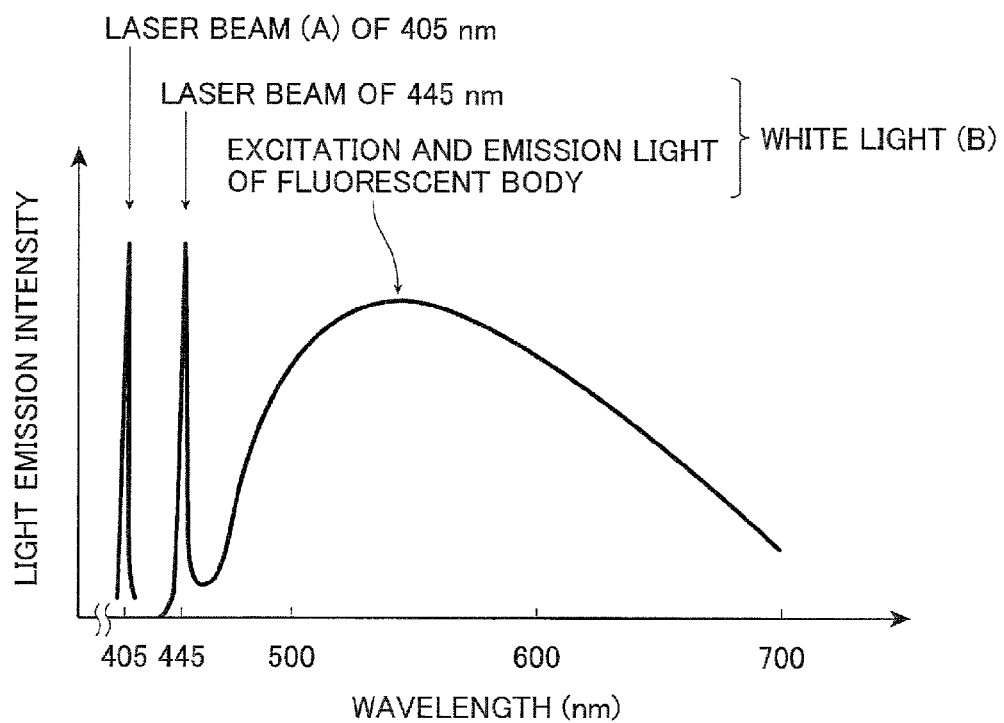
FIG. 2 is a graph illustrating emission spectrums of narrow band light emitted from a narrow band laser beam source and quasi-white light emitted from a white light source including a blue laser beam source and a fluorescent body used for a light source unit of the endoscope device shown in FIG. 1.

FIG. 2 is a graph illustrating emission spectrums of the blue-violet laser beam output from the blue-violet laser beam source 32, the blue laser beam output from the blue laser beam source 34, and the light obtained by converting the wavelength of the blue laser beam through the fluorescent body 24. The blue-violet laser beam is depicted by the emission line (profile A) having a central wavelength of 405 nm, is narrow band light of the invention, and is mainly used as special light. Further, the blue laser beam is depicted by the emission line having a central wavelength of 445 nm. The excitation and emission light obtained from the fluorescent body 24 using the blue laser beam substantially has a wavelength bandwidth of 450 nm to 700 nm, and has a spectral intensity distribution in which light emission intensity increases. By the profile B formed by the excitation and emission light and the blue laser beam, the above-described quasi-white light is formed, and is mainly used as ordinary light. Furthermore, although it is not shown in the drawings, the fluorescent body 24 is also excited by the blue-violet laser beam and emits excitation and emission light with a light amount of ⅛ of the case of the blue laser beam, so that it forms quasi-white light.

Here, the blue-violet laser beam with a central wavelength of 405 nm emitted from the blue-violet laser beam source 32 and the excitation and emission light from the fluorescent body 24 include a large amount of the component of the narrow band light of 405 nm and are excellently used to observe the surface layer tissue (acquire information on the surface layer tissue), but include a small amount of the excitation and emission light from the fluorescent body 24. For this reason, the light emission amount of the white light used for capturing the background may not be increased. Accordingly, when the distance up to the subject is close, the light emission amount of the white light for the background is sufficient. However, when the distance up to the subject is far, the light emission amount of the white light is not sufficient in the excitation and emission light generated by the blue-violet laser beam.

Further, the blue laser beam with a central wavelength of 445 nm emitted from the blue laser beam source 34 and the excitation and emission light from the fluorescent body 24 are not excellent for observing the surface layer tissue compared to the blue-violet laser beam, but may strongly excite the fluorescent body 24 and increase the light emission amount of the white light for the background. Accordingly, even when the distance up to the subject is far, the light amount of the white light may be sufficiently ensured.

For this reason, when the distance up to the subject becomes far, the blue laser beam source 34 may be used to compensate the light amount of the white light formed by the blue-violet laser beam from the blue-violet laser beam source 32.

Here, the white light mentioned in the invention is not precisely limited to the light including all wavelength components of the visible light, but may include, for example, light of a specific wavelength such as R, G, and B including the above-described quasi-white light. In a broad sense, for example, light including green to red wavelength components or light including blue to green wavelength components is included.

In the endoscope device 10, the light emission intensities of the profile A and the profile B are controlled to be relatively increased and decreased by the light source control section 48, so that an illumination port with an arbitrary luminance balance may be generated. Furthermore, in the endoscope device 10 of the invention, only the light of the profile B is used in the ordinary light mode, and in principle, the light of the profile A and the excitation and emission light (not shown) based on the light of the profile A are used in the special light mode. Here, in order to compensate the insufficient light amount of the excitation and emission light (not shown), the light of the profile B is overlapped.

As described above, the illumination light including the narrow band light (profile A) formed by the blue-violet laser beam from the blue-violet laser beam source (hereinafter, referred to as 405LD) 32 and the white light formed by the excitation and emission light (not shown) from the fluorescent body 24, and the illumination light (profile B) including the blue laser beam from the blue laser beam source (hereinafter, referred to as 445LD) 34 and the white light formed by the excitation and emission light from the fluorescent body 24 are emitted from the irradiation port 28A of the endoscope 12 toward the subject observation region of the subject. Then, the light returned from the subject observation region after emitting the illumination light thereto is formed on the light receiving surface of the imaging element 26 through the light receiving portion 28B, and the subject observation region is captured by the imaging element 26.

The image signal of the captured image output from the imaging element 26 after the imaging operation is input to an image processing system 36 of the processor 16 through a scope cable 30.

Next, the image signal of the image captured by the imaging element 26 in this manner is processed by the signal processing system including the image processing system 36 of the processor 16, is output to a monitor 38 or a recording device 42, and is provided for the user's observation.

Figure 3:
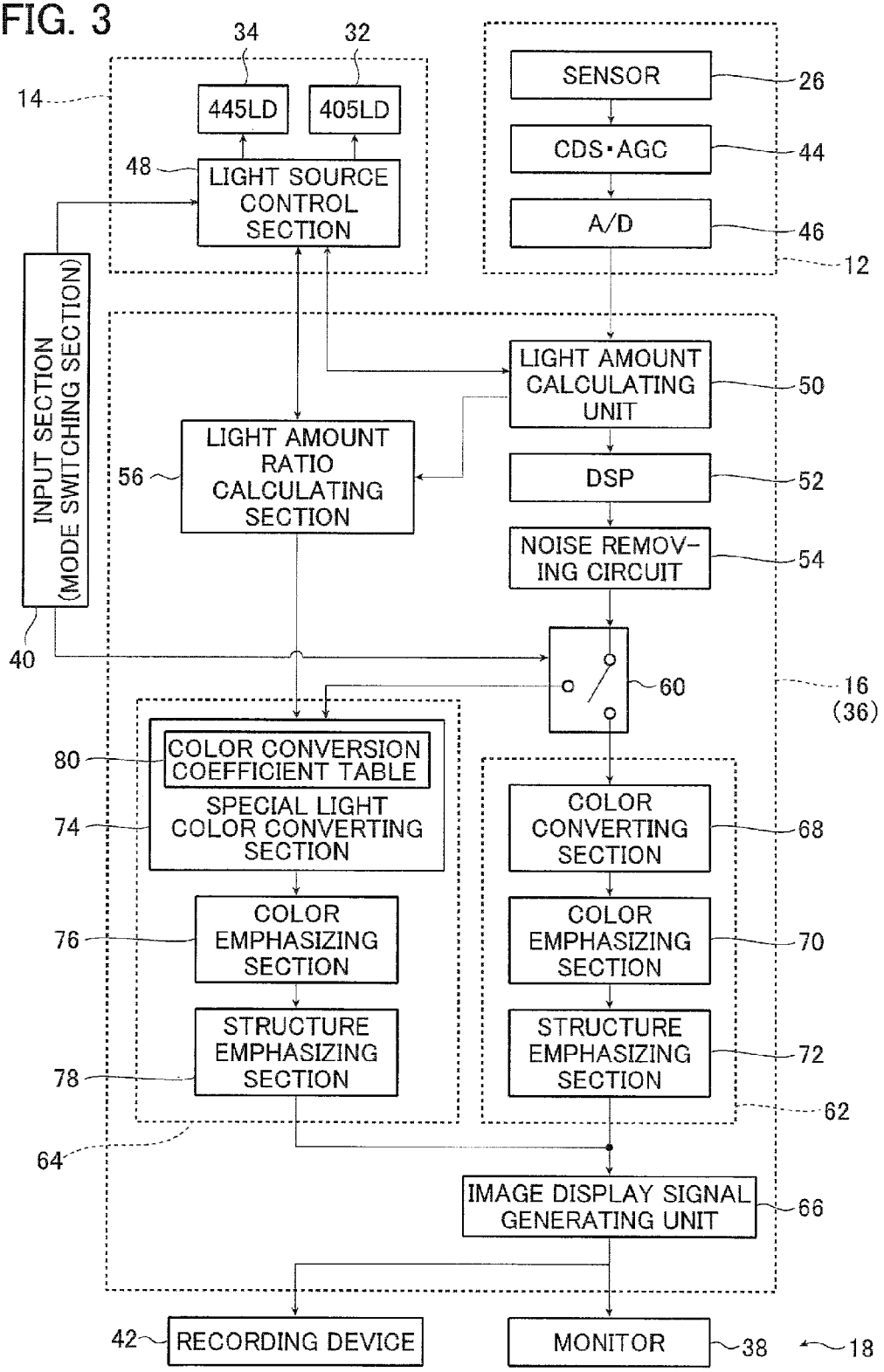
FIG. 3 is a block diagram illustrating a signal processing system for respective sections including a specific configuration of an example of a processor of the endoscope device shown in FIG. 1.

FIG. 3 is a block diagram illustrating the signal processing system for respective sections including a specific configuration of an example of the process of the endoscope device of the invention.

As shown in the same drawing, the signal processing system of the endoscope device 10 includes the signal processing system of the endoscope 12, the signal processing system of the light source unit 14, the signal processing system (image processing system 36) of the processor 16, the monitor 38 of the input and output unit 18, the input section (mode switching section) 40, and the recording device 42.

The signal processing system of the endoscope 12 is a signal processing system of an image signal of a captured image from the imaging element 26 after the imaging operation, and includes a CDS and AGC circuit 44 that performs a correlated double sampling (CDS) or an automatic gain control (AGC) on a captured image signal as an analog signal and an A/D converter 46 that converts the analog image signal subjected to the sampling and the gain control in the CDS and AGC circuit 44 into a digital image signal. The digital image signal A/D converted in the A/D converter 46 is input to the image processing system 36 of the processor 16 through the connector.

Further, the signal processing system of the light source unit 14 includes the light source control section 48 that performs a light amount control and an on/off control of the blue laser beam source (445LD) 34 and the blue-violet laser beam source (405LD) 32.

Here, the light source control section 48 turns on the blue-violet laser beam source 32 in response to a light source on signal generated when starting the operation of the endoscope device 10, controls an on and off state of the blue-violet laser beam source 32 in response to a signal output from the mode switching section 40 to switch to the special light mode or the ordinary light mode, or controls the light emission amount of the blue-violet laser beam source 32 and the blue laser beam source 34, that is, the value of the current flowing to the light sources 32 and 34 in accordance with the luminance value of the image calculated from a light amount calculating unit 50 to be described later. That is, the light source control section 48 serves as a light amount ratio changing unit together with the light amount calculating unit 50 and the light amount ratio calculating section 56 to be described later on the basis of the ratio between the calculated light emission amount and the light emission amount so as to change a light emission condition, that is, a light amount ratio between both light sources 32 and 34.

Furthermore, the signal processing system of the processor 16 is the image processing system 36 (refer to FIG. 1), and includes the light amount calculating unit 50, a DSP (digital signal processor) 52, a noise removing circuit 54, a light amount ratio calculating section 56, an image processing switching section (switch) 60, an ordinary light image processing unit 62, a special light image processing unit 64, and an image display signal generating unit 66.

The light amount calculating unit 50 uses the digital image signal input from the A/D converter 46 of the endoscope 12 through the connector, and calculates the light amount of the returned light received at the imaging element 26, that is, the luminance value of the captured image. Then, the calculated light amount is output to the light source control section 48 and the light amount ratio calculating section 56.

When the calculated light amount does not reach a predetermined value, the light source control section 48 controls the light emission amount of the blue-violet laser beam source (405LD) 32 and the blue laser beam source (445LD) 34 so that the light amount of the returned light become the predetermined value or more.

In the control of the light emission amount, first, the position between the front end of the endoscope and the subject is fixed, and the blue laser beam source (445LD) 34 is stopped to increase the light emission amount of the blue-violet laser beam source (405LD) 32 (refer to FIG. 4A).

When the calculated light amount of the returned light becomes the predetermined value or more, the subject is captured at the light emission amount. Further, when the light emission amount of the blue-violet laser beam source (405LD) 32 becomes maximal, but the light amount of the returned light is not sufficient, as shown in FIG. 4B, the blue laser beam source (445LD) 34 is turned on to increase the light emission amount as a whole. When the calculated light amount of the returned light becomes the predetermined value or more, the subject is captured at the light emission amount.

In general, even when the light emission amount of the blue-violet laser beam source (405LD) 32 as the light source of the narrow band light is not large and the light emission amount of the blue-violet laser beam source (405LD) 32 is maximal, the light emission amount thereof is limited. Accordingly, when the endoscope becomes farther from the subject, the light amount of the returned light detected at the imaging element is not sufficient. Further, in the general endoscope, the white illumination light source (here, the blue laser beam source (445LD) 34) is used for the ordinary light observation. Accordingly, in many cases, one lamp, two lamps, or three lamps are used, whereby the light emission amount may be sufficiently increased.

When the irradiation light amount of the blue laser beam source (445LD) 34 increases, the light amount is sufficient. However, the tone of the captured image changes, and the information of the captured image for the microstructure of the surface layer blood vessel subjected to the special light observation may not be visually obtained. Accordingly, there is a need to perform appropriately necessary contents of the image processing in the image processing unit to be described later.

Further, as described above, the light emission amount is controlled by fixing the position between the front end of the endoscope and the subject in order to obtain the light amount of the returned light necessary for a capturing operation, but the position of the front end of the endoscope may be moved with the fixed light emission amount.

For example, the light emission amount of the blue-violet laser beam source (405LD) 32 may be fixed to a predetermined value, and the endoscope may be moved to adjust the position between the front end of the endoscope and the subject so that the light amount of the returned light becomes the predetermined value or more.

Of course, when a capturing operation is performed at a position which may be expected that the light amount of only the blue-violet laser beam source (405LD) 32 is not sufficient, the light emission amount of the blue-violet laser beam source (405LD) 32 may be set to be maximal in advance, the light emission amount of the blue laser beam source (445LD) 34 may be fixed to a predetermined value, and as described above, the endoscope may be moved to adjust the position between the front end of the endoscope and the subject so that the light amount of the returned light becomes the predetermined value or more.

The light amount ratio calculating section 56 calculates the light amount ratio between the light emission amounts of the 405LD 32 and the 445LD 34 by receiving information on a current value of a current driving the blue-violet laser beam source (405LD) 32 and the blue laser beam source (445LD) 34 using the light source control section 48. The calculated light amount ratio is output to a special light color converting section 74 to be described later of the special light image processing unit 64.

Furthermore, when the light amount ratio of the laser changes, the white balance of the captured image changes. For this reason, although it is not shown in the drawings, a signal processing system may be configured in a manner such that the light amount and the light amount ratio of the 405LD 32 and the 445LD 34 are output to the CDS and AGC circuit 44 and the gain of the CDS and AGC circuit 44 obtaining the white balance on the basis of the information of the light amount and the light amount ratio so as to change the electric gain of the imaging element 26.

Further, although it is not shown in the drawings, the information of the gain for determining the white balance is output to the image processing unit 62 and the special light image processing unit 64, so that it is used for the color conversion and the special light color conversion.

The DSP 52 (digital signal processor) performs a gamma correction process and a color correction process on the digital image signal output from the A/D converter 46 after detecting the light source light amount at the light amount calculating unit 50.

The noise removing circuit 54 removes noise from the digital image signal subjected to the gamma correction process and the color correction process in the DSP 52 by performing, for example, a noise removing method in the image processing such as a moving-average method or a median filtering method.

In this manner, the digital image signal input from the endoscope 12 to the processor 16 is subjected to a pre-process such as a gamma correction process, a color correction process, and a noise removing process at the DSP 52 and the noise removing circuit 54.

The image processing switching section 60 is a switch that switches the transmission destination of the digital image signal subjected to a pre-process to the special light image processing unit 64 or the ordinary light image processing unit 62 at the rear stage on the basis of the instruction (switching signal) of the mode switching section (input section) to be described later.

Furthermore, in the invention, the digital image signal before the image processing using the ordinary light image processing unit 62 and the special light image processing unit 64 is referred to as an image signal, and the digital image signal before and after the image processing is referred to as image data.

The ordinary light image processing unit 62 is a unit that performs ordinary light image processing suitable for the digital image signal subjected to the pre-process using the white light (profile B) of the fluorescent body 24 and the 445LD in the ordinary light mode, and includes a color converting section 68, a color emphasizing section 70, and a structure emphasizing section 72.

The color converting section 68 performs a color conversion process such as a three-dimensional LUT process, a grayscale conversion process, and a three by three matrix process on the digital image signals of RGB three channels subjected to the pre-process, so that it is converted into RGB image data subjected to the color conversion process.

The color emphasizing section 70 is used to emphasize the blood vessel so as to be easily viewed by making a difference in color tint or hue between the blood vessel and the mucous in the screen, and performs a process on the RGB image data subjected to the color conversion process while seeing the screen. The process is, for example, a process that emphasizes a difference in color tint (hue) between the blood vessel and the mucous from the average value while seeing the average color tint of the entire screen.

The structure emphasizing section 72 performs a structure emphasizing process such as a sharpening process or an outline emphasizing process on the RGB image data subjected to the color emphasizing process.

The RGB image data subjected to the structure emphasizing process in the structure emphasizing section 72 is input as the RGB image data subjected to the ordinary light image processing from the ordinary light image processing unit 62 to the image display signal generating unit 66.

The special light image processing unit 64 is a unit that performs special light image processing suitable for the digital image signal subjected to the pre-process using the white light (profile B) from the fluorescent body 24 and the 445LD 34, and the blue-violet laser beam (profile A) from the 405LD 34 in the special light mode, and includes a special light color converting section 74, a color emphasizing section 76, and a structure emphasizing section 78.

The special light color converting section 74 allocates the G-image signal of the digital image signals of the RGB three channels subjected to the pre-process to the R-image data through a predetermined coefficient, and allocates the B-image signal to the G-image data and B-image data through a predetermined coefficient so as to generate the RGB image data. Then, the generated RGB image data is subjected to a color conversion process such as a three-dimensional LUT process, a grayscale conversion process, and a three by three matrix process as in the color converting section 68.

Specifically, the special light color converting section 74 normalizes the luminance for the allocated R, G, and B image data to generate $R_{norm}$, $G_{norm}$, and $B_{norm}$ image data. Next, the special light color converting section performs a correction on the normalized $R_{norm}$, $G_{norm}$, and $B_{norm}$ image data with a tone in accordance with the light amount ratio. When the image data subjected to the adjustment of tone is set to $R_{adj}$, $G_{adj}$, and $B_{adj}$ image data, the $R_{adj}$, $G_{adj}$, and $B_{adj}$ image data subjected to the adjustment of tone may be obtained by the calculation shown in Equation (1).

$$(R_{adj}, G_{adj}, B_{adj}) = (K_R, K_G, K_B) \begin{pmatrix} R_{norm} \\ G_{norm} \\ B_{norm} \end{pmatrix} \quad (1)$$

Here, $K_R$, $K_G$, and $K_B$ respectively denote color conversion coefficients of respective colors, and may be obtained in accordance with the light amount ratio calculated in the light amount ratio calculating section 56. As shown in FIG. 5, the special light color converting section 74 includes a color conversion coefficient table 80 in which the color conversion coefficients of respective colors corresponding to the light amount ratio are determined, and determines the color conversion coefficients $K_R$, $K_G$, and $K_B$ on the basis of the calculated light amount ratio with reference to the color conversion coefficient table 80. As shown in FIG. 5, the color conversion coefficients $K_R$, $K_G$, and $K_B$ of the color conversion coefficient table 80 are respectively set to $R_{00\sim}$, $G_{00\sim}$, and $B_{00\sim}$ so as to correspond to the light amount ratio. When the color conversion coefficient corresponding to the light amount ratio calculated in the light amount ratio calculating section 56 is applied to Equation (1), the image data $R_{adj}$, $G_{adj}$, and $B_{adj}$ subjected to the adjustment of tone may be obtained.

For example, the ratio between the light amount of the 405LD 32 and the light amount of the 445LD 34 controlled by the light source control section 48 is 100:10, that is, the light amount ratio is 405LD:445LD≈90.9:9.1, the color conversion coefficient may be obtained as $(K_R, K_G, K_B) = (R_{10}, G_{10}, B_{10})$ from the color conversion coefficient table shown in FIG. 5.

The color conversion coefficient is not limited to the table shown in FIG. 5, but may be expressed by mathematization or may be obtained in a manner such that only representative points are numerically converted and the other points are obtained by an interpolation calculation.

As in the color emphasizing section 70, the color emphasizing section 76 is used to emphasize the blood vessel so as to be easily viewed by making a difference in color tint between the blood vessel and the mucous in the screen, and performs a process on the RGB image data subjected to the color conversion process while seeing the screen. The process is, for example, a process that emphasizes a difference in color tint between the blood vessel and the mucous from the average value while seeing the average color tint of the entire screen.

The structure emphasizing section 78 performs a structure process such as a sharpening process or an outline emphasizing process on the RGB image data subjected to the color emphasizing process as in the structure emphasizing section 72.

The RGB image data subjected to an optimal frequency emphasizing process in the structure emphasizing section 78 is output as RGB image data subjected to the special light image processing from the special light image processing unit 64 to the image display signal generating unit 66.

Further, as described above, when the light amount is not sufficient and the light emission amount of the blue laser beam source (445LD) 34 increases, the light amount for the capturing operation is sufficient. However, the tone of the captured image changes, and the information of the captured image for the microstructure of the surface layer blood vessel as the special light observation is not visually obtained.

Therefore, the special light image processing unit 64 may perform a frame summing process or a binning process at the previous step of the color converting section 68 in order to emphasize the surface layer blood vessel of the captured image.

Here, the frame summing process generally indicates a process of summing a plurality of frames each forming one image, and the binning process indicates a process of combining a plurality of pixels forming an image.

Furthermore, instead of the frame summing process and the binning process, the charge ambulation time of the imaging element 26 may be lengthened in advance. Accordingly, the substantially same effect is obtained as that of the frame summing process.

The image display signal generating unit 66 converts the RGB image data subjected to the image processing input from the ordinary light image processing unit 62 in the ordinary light mode and the RGB image data subjected to the image processing input from the special light image processing unit 64 in the special light mode into a display image signal to be displayed as a soft copy image in the monitor 38 or a display image signal to be output as a hard copy image in the recording device 42.

The monitor 38 displays the soft copy image, that is, the ordinary observation image based on the display image signal obtained in the imaging element 26 by emitting the white light and subjected to the pre-process and the ordinary light image processing in the processor 16 in the ordinary light mode, and displays the soft copy image, that is, the special light observation image based on the display image signal obtained in the imaging element 26 by emitting the special light in accordance with the white light and subjected to the pre-process and the special light image processing in the processor 16 in the special light observation mode.

The recording device 42 also outputs the hard copy image, that is, the ordinary observation image obtained by emitting the white light in the ordinary light mode, and outputs the hard copy image, that is, the special light observation image obtained by emitting the white light and the special light in the special light mode.

Furthermore, if necessary, the display image signal generated in the image display signal generating unit 66 may be stored as image information in a storage unit including a memory or a storage device (not shown).

On the other hand, the mode switching section (input section) 40 includes a mode switching button that switches the ordinary light mode and the special light mode, and the mode switching signal from the mode switching section 40 is input to the light source control section 48 of the light source unit 14. Here, the mode switching section 40 is disposed as the input section 40 of the input and output unit 18, but may be disposed at the processor 16, the operation section of the endoscope 12, or the light source unit 14. Furthermore, the switching signal from the mode switching section 40 is output to the light source control section 48 and the image processing switching section 60.

The endoscope device of the invention basically has the above-described configuration.

Hereinafter, an operation of the endoscope device of the invention will be described by referring to FIGS. 6 and 7.

In the embodiment, first, it is assumed that the ordinary light observation is performed in the ordinary light mode. That is, the 445LD 34 is turned on, and the ordinary light image processing is performed on the captured image data using the white light in the ordinary light image processing unit 64.

Figure 6:
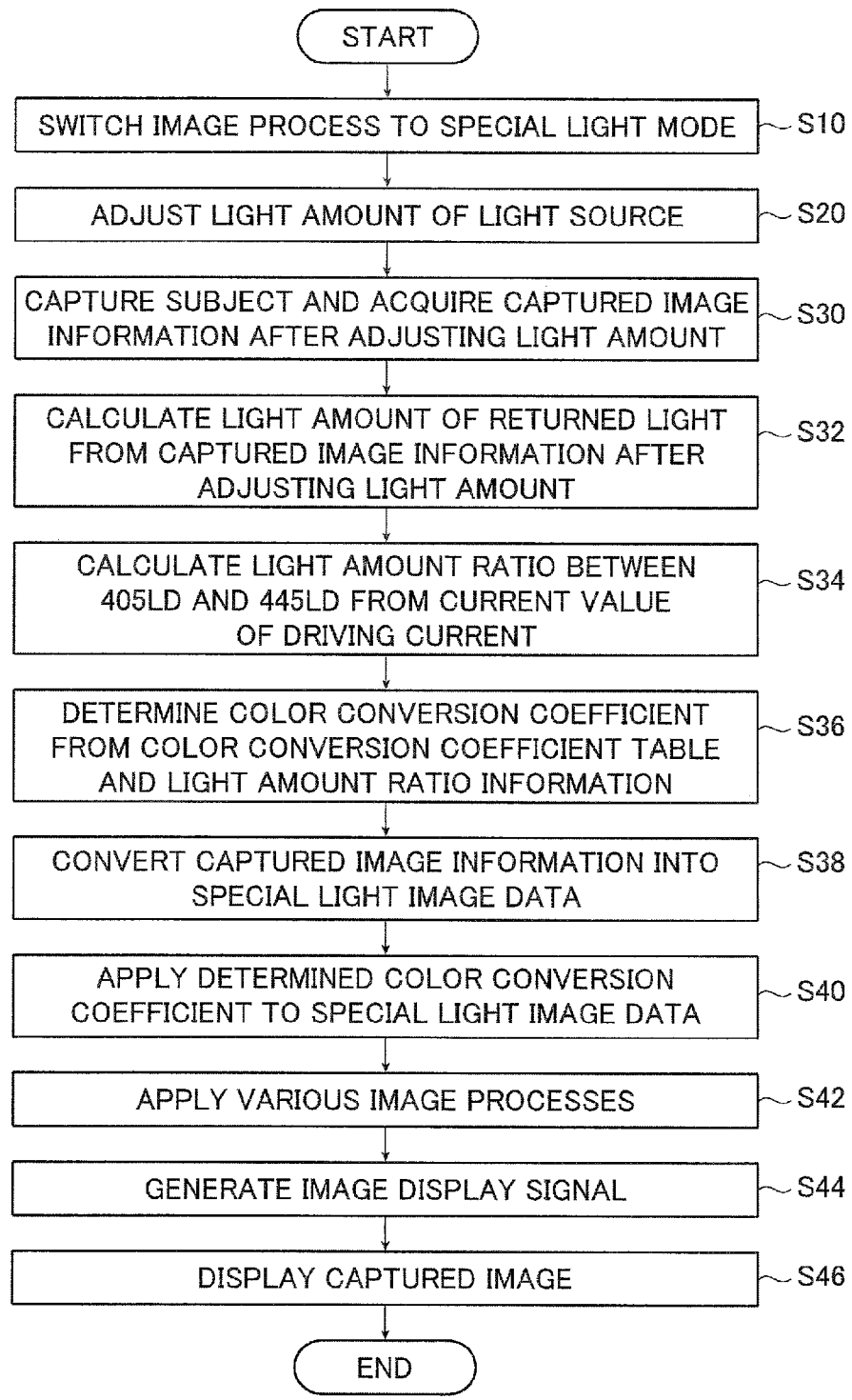
FIG. 6 is a flowchart illustrating a flow of an example of a special light observation performed by the endoscope device shown in FIG. 1.

Here, according to the steps shown in FIG. 6, the special light mode is switched by a user. When the user operates the mode switching section 40, a mode switching signal (special light ON) is output, and the image processing in the image processing switching section 60 is switched to the special light mode (S10).

When the special light mode is switched, the light amount of the light source is adjusted (S20). There is a need to perform an adjustment of the light emission amount from the light source in accordance with a variation in positional relation between the front end of the endoscope and the subject. The adjustment of the light amount of the light source when fixing the position between the front end the endoscope and the subject is performed according to the steps shown in FIG. 7.

First, a predetermined amount of narrow band light (405 nm) is emitted from the blue-violet laser beam (405LD) 32, and narrow band light (405 nm) and excitation and emission light thereof are emitted as illumination light from the front end of the endoscope toward the subject (S120).

The emitted illumination light is reflected by the subject, and the returned light is acquired as captured image information by the imaging element 26 (S122).

When the captured image information is acquired, the captured image information is output to the light amount calculating unit 50 through the CDS and AGC circuit 44 and the A/D converter 46, and the light amount (the luminance value of the captured image) of the returned light at the imaging element 26 is calculated (S124). The calculated light amount of the returned light is output to the light source control section 48.

The light source control section 48 determines whether the light amount is sufficient on the basis of the light amount calculated at the light amount calculating unit 56, that is, the light amount of the returned light is a predetermined value or more (S126). When the light amount is sufficient, the irradiation light amount at that position does not need to be performed, and the subject is captured as shown in FIG. 6 without adjusting the light amount of the light source (S30). Of course, when the light amount is too much, so that an overflow occurs in the imaging element 26, a control is performed so that the current value of the driving current flowing to the 405LD 32 is decreased.

Further, when the light amount is not sufficient, the light source control section 48 determines whether the output of the 405LD 32 is maximal from the current value of the driving current flowing to the 405LD 32 (S128).

When the output of the 405LD is not maximal, the light source control section 48 increases the output (the current value of the driving current) of the 405LD 32 (S130), and calculates the light amount again (S124).

Further, when the output of the 405LD 32 is maximal, the light source control section 48 determines whether the blue laser beam source (445LD) 34 is turned on (S132). When the 445LD 34 is not turned on, the 445LD 34 is turned on (S134), and the light amount is calculated again (S124). When the 445LD 34 is turned on, the narrow band light (405 nm) and the excitation and emission light thereof as illumination light overlap each other, and the narrow band light (445 nm) and the excitation and emission light thereof are emitted from the front end of the endoscope to the subject.

Further, when the 445LD 34 is already turned on, the output of the 445LD 34 is increased (S136), and the light amount is calculated again (S124).

In this manner, the light emission amount is adjusted on the basis of the steps shown in FIG. 7 until the light amount of the returned light at the imaging element 26 becomes a predetermined value or more. Furthermore, although it is not described in the steps of FIG. 7, when the light amount is not sufficient even after maximally increasing the output of the 445LD 34, the subject is directly captured as shown in FIG. 6 (S30) or the position between the front end of the endoscope and the subject is adjusted again so as to move the front end of the endoscope close to the subject.

Here, described is an operation of adjusting the light amount when the position between the front end of the endoscope and the subject is fixed. However, as described above, the light emission amount from the light source may be fixed, and the position between the front end of the endoscope and the subject may be changed.

In this case, as described above, two operations may be supposed. One is a case in which the light emission amount of the 405LD 32 is set to a predetermined value, the 445LD 34 is stopped, and the positional relation between the front end of the endoscope and the subject is changed. Then, the other is a case in which the light emission amount of the 405LD 32 is set to be maximal, the light emission amount of the 445LD 34 is set to a predetermined value, and the positional relation between the front end of the endoscope and the subject is changed. The case of only using the 405LD 32 is mainly used for a case where a capturing operation is performed by moving the front end of the endoscope and the subject close to each other. The case of setting the light emission amount of the 405LD 32 to be maximal and setting the light emission amount of the 445LD 34 to a predetermined value is mainly used for a case where a capturing operation is performed by moving the front end of the endoscope and the subject far from each other.

Then, when the light amount is adjusted as shown in FIG. 7 (S20), the subject is captured, and the captured image information is acquired by the imaging element 26 (S30). As described above, the captured image information is appropriately processed by the CDS and AGC circuit 44 and the A/D converter 36, and is output to the light amount calculating unit 56.

In the light amount calculating unit 56, the light amount of B light and the light amount of G light are respectively calculated from the captured image information, and are output to the light amount ratio calculating section 56 (S32). Further, the captured image information is output as a captured image signal to the special light image processing unit 64 through the DSP 52 and the noise removing circuit 54.

In the light amount ratio calculating section 56, the light emission amount of the 405LD 32 and the light emission amount of the 445LD 32 of the light source control section 48 are acquired, and the light amount ratio between the 405LD 32 and the 445LD 34 is calculated (S34). The calculated light amount ratio is output to the special light color converting section 74 of the special light image processing unit 64.

On the basis of the information of the light amount ratio, in the special light color converting section 74 of the special light image processing unit 64, the color conversion coefficients $k_R$, $k_G$, and $k_G$ used for the special light color conversion are set from the calculated light amount ratio information and the color conversion coefficient table 80, and the captured image signal input to the special light image processing unit 64 becomes predetermined RGB image data by the special light color converting section 74 (S36). Furthermore, an image emphasizing process such as a frame summing process may be performed before the special light color conversion.

Various contents of the image processing are performed on the RGB image data in the color emphasizing section 76 and the structure emphasizing section 78 and the result is output from the image display signal generating unit 66 in the form of an image display signal which may be displayed on the monitor 38 or the like (S38).

The output image display signal is displayed as a special light image on the monitor 38, and is recorded in the recording device 42 (S40).

While the endoscope device of the invention has been described in detail, the invention is not limited to the above-described embodiment, and various modifications or changes may be performed within the scope without departing from the spirit of the invention.

What is claimed is:

1. An endoscope device comprising:
    a first light source section that emits narrow band light having a predetermined wavelength bandwidth narrowed in accordance with spectral spectrum characteristics of a structure and a component of a living body as a subject;
    a second light source section that emits wide band light having a wide wavelength bandwidth including a visible region, the first and second light source sections being used for a special light observation of the subject using the narrow band light and the wide band light;
    a light source control section that controls light emission amounts of said narrow band light from said first light source section and said wide band light from said second light source section and light emission amounts of said narrow band light and said wide band light;
    an imaging section that captures an image of said subject for the special light observation of the subject using returned light of illumination light in which at least one of the illumination light comprising said narrow band light and said wide band light emitted to said subject is reflected and returned from said subject and outputs captured image information for the special light observation of the subject;
    a light amount calculating section that calculates a light amount of said returned light as a capturing light amount of the captured image from said captured image information captured by said imaging section;
    a light amount ratio calculating section that calculates a ratio between a light emission amount of said narrow band light emitted from said first light source section and a light emission amount of said wide band light emitted from said second light source section controlled by said light source control section, the light emission amount of said wide band light being added to the illumination light in order to compensate an insufficient light emission amount of said narrow band light; and
    an image processing section that performs a predetermined image processing on said captured image information,
    wherein said light source control section controls the light emission amount of said narrow band light emitted from said first light source unit and the light emission amount of said wide band light emitted from said second light source section in accordance with said capturing light amount of said returned light calculated by said light amount calculating section so that said light amount of said returned light calculated by said light amount calculating section becomes a predetermined value or more necessary for capturing said subject for the special light observation of the subject, and
    wherein said imaging section outputs said captured image information a gain of which is adjusted so that a white balance of said captured image does not change in accordance with the light emission amount of said narrow band light, the light emission amount of said wide band light and the ratio between the light emission amount of said narrow band light and the light emission amount of said wide band light, and outputs an R-image signal, a G-image signal and a B-image signal as said captured image information when a red color, a green color and a blue color are represented by R, G, B respectively, and wherein said image processing section generates R-image data of a quasi-color image from the G-image signal outputted by said imaging section, and generates G-image data and B-image data of the quasi-color image from the B-image signal outputted by said imaging section, and performs tone correction on the generated R-image data, the generated G-image data and the generated B-image data of said quasi-color image in accordance with said ratio between the light emission amount of said narrow band light and the light emission amount of said wide band light calculated by said light amount ratio calculating section to change an image processing condition for adjusting a color tint of the quasi-color image for the special light observation of the subject.

2. The endoscope device according to claim 1, wherein said light source control section performs different controls the light emission amount of said wide band light emitted from said second light source section in accordance with said capturing light amount of said returned light calculated by said light amount calculating section such that: in case of a capturing operation using said narrow band light, emission of said wide band light from said second light source section is stopped and then that said light source control section controls the light emission amount of said narrow band light emitted from said first light source section is controlled and, when so that the light emission amount of said narrow band light becomes maximal, said wide band light is emitted from said second light source section and then the light emission amount of said wide band light is controlled, and in case of a capturing operation without using said narrow band light, emission of said narrow band light from said first light source section is stopped and then the light emission amount of said wide band light emitted from said second light source section is controlled.

3. The endoscope device according to claim 1, wherein said light source control section controls at least one of the light emission amount of said narrow band light from said first light source section and the light emission amount of said wide band light from said second light source section so that said capturing light amount of said returned light calculated by said light amount calculating section substantially becomes equal to a the predetermined value necessary for capturing said subject regardless of a distance between said imaging section and said subject for the special light observation of the subject.

4. The endoscope device according to claim 1, wherein said image processing section includes a color conversion coefficient table representing a relationship between a color conversion coefficient for adjusting a the color tint of the captured quasi-color image and a the ratio between the light emission amount of said narrow band light and the light emission amount of said wide band light obtained in advance so that a white balance of said captured image does not change, in order to change said image processing condition, and said image processing section selects said color conversion coefficient from said color conversion coefficient table based on said ratio between the light emission amount of said narrow band light and the light emission amount of said wide band light calculated by said light amount calculating section.

5. The endoscope device according to claim 1, wherein said image processing section changes the image processing condition so as to compensate for change in the color tint of the quasi-color by adding said wide band light in accordance with the ratio between the light emission amount of said narrow band light and the light emission amount of said wide band light.

6. The endoscope device according to claim 1, wherein said image processing section generates the R-image data of the quasi-color image by allocating the G-image signal outputted by said imaging section to R-image data through a predetermined coefficient, and generates the G-image data and the B-image data of the quasi-color image by allocating the B-image signal outputted by said imaging section to G-image data and B-image data through predetermined coefficients, respectively.

7. The endoscope device according to claim 1, wherein said imaging section calculates $R_{adj}$, $G_{adj}$ and $B_{adj}$ using the following Equation (1), when the R-image signal, the G-image signal and the B-image signal are represented by $R_{norm}$, $G_{norm}$ and $B_{norm}$, respectively, the R-image data, the G-image data and the B-image data of the quasi-color image subjected to the tone correction are represented by $R_{adj}$, $G_{adj}$ and $B_{adj}$, respectively, and respective color conversion coefficients of R, G and B colours for adjusting the color tint of the quasi-color image are represented by $K_R$, $K_G$ and $K_B$.

$$(R_{adj}, G_{adj}, B_{adj}) = (K_R, K_G, K_B)\begin{pmatrix} R_{norm} \\ G_{norm} \\ B_{norm} \end{pmatrix}. \quad (1)$$

8. The endoscope device according to claim 7, wherein said image processing section includes a color conversion coefficient table representing a relationship between the color conversion coefficients $K_R$, $K_G$ and $K_B$ for adjusting the color tint of the quasi-color image and the ratio between the light emission amount of said narrow band light and the light emission amount of said wide band light obtained in advance in order to change said image processing condition, and said image processing section selects said color conversion coefficients $K_R$, $K_G$ and $K_B$ from said color conversion coefficient table based on said ratio between the light emission amount of said narrow band light and the light emission amount of said wide band light calculated by said light amount calculating section.

* * * * *